United States Patent [19]

Carlin et al.

[11] Patent Number: 4,996,222

[45] Date of Patent: Feb. 26, 1991

[54] PHARMACEUTICAL FORMULATIONS

[75] Inventors: Brian A. C. Carlin, Baldock; John N. C. Healey, Hitchin; Graham S. Leonard, St. Albans; Geoffrey D. Tovey, Harpenden, all of England

[73] Assignee: Smith Kline & French Laboratories Limited, Welwyn Garden City, United Kingdom

[21] Appl. No.: 490,851

[22] Filed: Mar. 9, 1990

Related U.S. Application Data

[63] Continuation of Ser. No. 79,198, Jul. 29, 1987, abandoned.

[51] Int. Cl.⁵ .......................................... A61K 31/415
[52] U.S. Cl. ................................................... 514/400
[58] Field of Search ......................................... 514/400

[56] References Cited

FOREIGN PATENT DOCUMENTS 138540 4/1985 European Pat. Off. .
104868 8/1981 Japan .

Primary Examiner—Olik Chaudhuri
Assistant Examiner—Ellen McAvoy
Attorney, Agent, or Firm—Dara L. Dinner; Edward T. Lentz; Stuart R. Suter

[57] ABSTRACT

The invention provides pharmaceutical suspension compositions of cimetidine wherein substantially all of the cimetidine is in the polymorph B crystalline form.

16 Claims, No Drawings

PHARMACEUTICAL FORMULATIONS

This is a continuation of application Ser. No. 07/079,198 filed July 29, 1987, now abandoned.

This invention relates to new pharmaceutical compositions and methods for their preparation, and in particular it relates to suspensions comprising cimetidine.

Cimetidine is a histamine $H_2$-antagonist which has been used for a number of years in the treatment of duodenal and benign gastric ulceration, recurrent and stomal ulceration, oesophageal reflux disease and other conditions where reduction of gastric acid by cimetidine has been shown to be beneficial, for example persistent dyspeptic symptoms with or without ulceration. It is widely recognised that there are considerable technical difficulties in producing stable and acceptable pharmaceutical compositions of cimetidine, particularly liquid solution and suspension compositions. Firstly, there is the difficulty of polymorphism which gives rise to problems of polymorphic transitions and crystal growth. It is generally recognised that cimetidine can exist in at least 5 different polymorphic forms and that these polymorphic forms differ in crystal habit and crystallisation properties, thermodynamic stability, and solubility and rate of dissolution in water. It is generally recognised that the polymorphic form A has been used almost exclusively in compositions. B. Hegedüs and S. Görög, *J. Pharmaceutical & Biomedical Analysis*, Vol. 3, No. 4, pp.303-313, 1985. Secondly, there is the problem that cimetidine has a very bitter taste and palatability of oral compositions is a major consideration.

It is clear that there has been a need for compositions of cimetidine which are liquid based and are palatable. Cimetidine is absorbed almost exclusively in the small intestine and liquid-based compositions offer the possibility that they could be absorbed more quickly and more efficiently than tablet compositions, particularly tablet compositions which have been coated to minimise unpleasant tastes. However, with solutions of cimetidine, the unpleasant bitter taste is a particular problem. Suspensions of cimetidine could in principle offer the advantage of being more palatable but until recently no stable suspension compositions of cimetidine have been described or sold. Some companies have tried to meet the apparent need for such a product by selling cimetidine powder or granules in sachets which can be extemporaneously mixed with water to produce suspension compositions.

EPA 0 138 540-A describes suspensions containing cimetidine and the preferred examples are buffered solutions of high viscosity. Because of the high viscosity, such suspensions are not easily poured from a bottle and consequently are usually formulated in sachets.

Aqueous suspensions of cimetidine polymorph A are thermodynamically unstable and it is found that when many such suspensions are prepared having relatively low viscosity, they are likely, when subjected to fluctuating temperatures, to undergo polymorphic transition into the polymorphic B form. This polymorphic transition, forms polymorph B in situ as very long needle-like crystals, which makes the suspensions lumpy and non-homogeneous thereby introducing dosage inaccuracy and giving rise to an unpleasant mouth feel.

It is an object of this invention to provide a suspension of cimetidine which is stable and, in particular, is of relatively low viscosity such that it can be easily poured from bottle and easily administered using a spoon or like device so that various dosages can be exactly and accurately measured. It is also an object of this invention to form a stable composition to which other ingredients such as antacids or alginates can be added.

We have now found that by preparing suspensions from cimetidine polymorph B, the problem of polymorphic transition and the growth in situ of long needle-like crystals can be avoided.

According to the invention, there is provided a stable pharmaceutical composition suitable for oral administration comprising a suspension of particulate cimetidine in an aqueous phase having a pH of at least 7, and a suspending agent, wherein substantially all of the cimetidine present is of the polymorphic B form, and optionally any other pharmaceutical excipients.

Preferably at least 90% and particularly preferably at least 95% of the cimetidine is in the polymorphic B form. It is preferred that substantially no polymorph A is present.

By stable is meant a suspension which is capable of remaining in a pharmaceutically acceptable condition for a prolonged period, for example at least six months, preferably at least a year and most preferably for more than three years. Thus there should not be significant crystal growth, and any sediment formed should be capable of being re-suspended with only mild agitation, i.e. the sediment should not take the form of a "cake" or lumps which cannot readily be re-suspended. Preferably no sediment should form at all.

It is in general preferred that the pH of the suspension is within the range 7-9.5, preferably 7.4-8.4, and particularly 7.8-8.2. It will be appreciated that the suspensions can be either buffered or unbuffered.

It is preferred that the suspensions of the present invention have a viscosity of less than 1,500 mPa.s but greater than 200 mPa.s, for example within the range 1,200 mPa.s to 500mPa.s. The skilled man will be aware that the viscosity values obtained for a given system depend on the temperature, the shear rate and the shear history. The above figures refer to freshly shaken and poured suspensions at approximately 25° C. subjected to a shear rate of 0.7 sec.$^{-1}$.

An advantage of suspensions having a viscosity within the range 200 mPa.s to 1,500 mPa.s is that they are readily pourable. This is in contrast to suspensions prepared from cimetidine polymorph A which frequently are required to be of a high viscosity in order to remain stable, i.e. to minimise polymorphic interconversion, the viscosity being such that they are not readily pourable. By readily pourable is meant that they are capable of being easily poured from a suitable container such as a bottle. It will be readily appreciated that where the composition is a reversible gel, it may be necessary to shake the container before pouring in order to disrupt the gel structure.

When the suspension contains alginate, the thickening effect of the alginate means that the viscosity of the suspension is generally higher than the range 200-1,500 mPa.s quoted above and typically is in the the range 2,500-5,000 mPa.s for example approximately 3,500 mPa.s.

Examples of suspending agents include xanthan gum, hydroxypropylmethylcellulose, methylcellulose, carageenan, sodium carboxymethyl cellulose, and sodium carboxymethyl cellulose/microcrystalline cellulose mixtures, particularly sodium carboxymethyl cellulose/microcrystalline cellulose mixtures. Preferred suspending agents are thixotropic suspending agents such as xanthan gum, carageenan and sodium carboxymethyl cellulose/microcrystalline cellulose mixtures and particularly preferred suspending agents are Avicel RC591, Avicel RC581 and Avicel CL611. Avicel is a trademark of FMC Corporation, and RC591, RC581 and CL611 are mixtures of microcrystalline cellulose and sodium carboxymethyl cellulose. The amount of suspendinq agent present will vary according to the particular suspending agent used and the presence or absence of other ingredients which have an ability to act as a suspending agent or which contribute significantly to the viscosity of the composition. In general, however, the amount of suspending agent will lie in the range 0.1–1.5% w/w of the total weight of the composition. When the suspending agent is xanthan gum, it will usually be present in an amount corresponding to 0.1–0.5% w/w of the total weight whereas when Avicel is used, the amount typically will lie in the range 0.6–1.5% w/w particularly approximately 1.2% w/w. When carageenan is used, typically this will constitute 0.5–1% w/w of the composition. Compositions containing alginate, which has a significant thickening effect, will, in general, contain lower concentrations of suspending agent in order to avoid the problem of the viscosity being so great that the composition cannot be poured.

The suspension can contain ingredients which improve its taste, for example sweeteners, bitter-taste maskers such as sodium chloride and taste-masking flavours such as contramarum, flavour enhancers such as monosodium glutamate, and flavouring agents.

Examples of sweeteners include bulk sweeteners such as sucrose, hydrogenated glucose syrup, the sugar alcohols sorbitol and xylitol, and sweetening agents such as sodium cyclamate, sodium saccharin, aspartame and ammonium glycyrrhizinate.

A bulk sweetener will usually be present in an amount corresponding to about 15–70% w/w of the total weight of the suspension, the amount depending in part upon whether other ingredients, e.g. alginate, are present which have a thickening effect on the composition. For example, when sorbitol is used as the sole bulk sweetener and no thickener (e.g. alqinate) is present, typically the dry weight of sorbitol present is in the range 35–55% w/w of the total weight of the suspension, for example at a concentration of approximately 45% w/w.

When hydrogenated glucose syrup (solids content approximately 74%) is used as the sole bulk sweetener, typically it is present as 55–70% w/w of the suspension, for example at a concentration of approximately 65% w/w (equivalent to 49% solids). It will be appreciated that combinations of bulk sweeteners can be used, for example combinations of sorbitol and hydrogenated glucose syrup, or sucrose and sorbitol.

Other excipients which can be used include humectants such as propylene glycol and glycerol and colourants such as titanium dioxide.

Typically the total quantity of humectant present is in the range 0–10% w/w. Thus, for example, propylene glycol and glycerol can each be present in an amount approximating to 4% w/w.

It is preferred that the suspensions contain preservatives to prevent microbial contamination. Examples of preservatives are the alkylparabens, particularly propylparaben and butylparaben. Parabens tend to be unstable at high pH values and hence most suitably are employed when the pH is below 8.2.

Preferably the suspension contains from 1.0 to 4.5% w/w cimetidine.

In one preferred embodiment of the invention there is provided a composition containing 1.5–3.5% w/w of cimetidine, 35–45% w/w of water, 35–55% of sorbitol, 0–10% w/w of a humectant which is propylene glycol and/or glycerol, 0.6–1.5% W/w of a mixture of sodium carboxymethyl cellulose and microcrystalline cellulose and optionally other pharmaceutical excipients.

The compositions of this invention can optionally contain an antacid. An antacid is a pharmaceutically acceptable basic material of sufficient neutralising capacity to neutralise stomach acid. Examples of antacids are aluminium hydroxide, magnesium hydroxide, magnesium carbonate, calcium carbonate and co-dried gels for example aluminium hydroxide-magnesium carbonate co-dried gel. Preferably the amount of antacid is such that a unit dose contains 10–30 milliequivalents.

In a further embodiment of the invention, there is provided a suspension of cimetidine polymorph B additionally containing alginate.

The purpose of the alginate is to form a raft of mucilage which floats on the contents of the stomach thereby preventing gastro-oesophageal reflux (GORD) or reducing its symptoms. Usually a carbonate salt such as potassium bicarbonate or sodium bicarbonate is added. Reaction of the carbonate with the acidic gastric juices generates carbon dioxide which aerates the alginate raft, reducing its density and thereby enabling it more easily to float on the stomach contents.

When bicarbonate salts are present, the suspensions are maintained at a pH of 7.5 or more in order to prevent premature decomposition and evolution of carbon dioxide. Typically the pH i$ maintained in the range 7.8–8.4, for example by using a buffering agent such as a phosphate buffer.

In order to avoid too great an increase in the viscosity of the suspension, a low viscosity grade of alginate is used. Low viscosity grades of alginate suitable for use in the compositions of the present invention will generally have a viscosity of 4–10 mPa.s in 1% aqueous solution at 20° C. Alginates are polymers composed of mannuronic and guluronic acid monomer units. The ratio of mannuronic to guluronic acids determines the raft-forming properties of the alginate and, in general, alginates having a high guluronic:mannuronic ratio (e.g. 70% guluronic acid) form the strongest rafts. Alginates containing such high levels of guluronic acid are preferably used in the compositions of the present invention, and one such alginate is Protanal LFR 5/60.

The concentration of alginate will be chosen so as to optimise the raft-forming ability of the suspension whilst not adversely affecting the pourability of the suspension by increasing the viscosity too much.

In practice, the concentration of alginate (w/w) typically is less than 10% relative to the total weight of the suspension. Preferably the alginate is present at a concentration of approximately 5%.

The alginate is usually present as an alkali metal salt such as sodium alginate.

A problem which has been encountered in the preparation of cimetidine alginate suspensions is that the cimetidine can be oxidised to its sulphoxide. Cimetidine sulphoxide is a known metabolite of cimetidine and whereas its presence in the suspension does not give rise to problems of toxicity, the sulphoxide is essentially inactive as an $H_2$-antagonist and thus the oxidation of cimetidine may lead to a reduction in efficacy of the composition.

The mechanism of sulphoxide formation is not known. The addition of standard antioxidants such as propyl gallate and sodium sulphite does not inhibit the formation of the sulphoxide. Moreover certain chelating agents such as polyphosphates and trisodium citrate have been added but have also been found to be ineffective in preventing oxidation. However, it has now surprisingly been found that sulphoxide formation can be significantly inhibited by the addition of ethylenediaminetetraacetic acid (EDTA) and salts thereof.

In a preferred aspect of this invention, therefore, there is provided a pharmaceutical suspension as hereinbefore defined comprising cimetidine polymorph B and, additionally, alginate and EDTA or a salt thereof. Typically the EDTA is present in an amount from approximately 0.05% (w/w) to approximately 0.25% (w/w) of the total weight of the suspension; particularly approximately 0.1% (w/w). The EDTA is usually added as a salt. Particularly the disodium salt.

In the compositions of the present invention, typically the particle size of the cimetidine is such that in the final suspension 80% by weight of the particles are less than $200\mu$ in size but are greater than approximately $5\mu$ in size. The sizes referred to are the apparent diameters as measured by a Malvern 3600E Laser particle Sizer (supplied by Malvern Instruments Limited, Spring Lane, Worcester, U.K.).

The compositions of the present invention can be prepared by mixing the cimetidine polymorph B with the suspending agent, and any other ingredients to be included, to form a suspension.

The cimetidine polymorph B can be prepared by forming a solution of cimetidine acetate in aqueous isopropanol (10% isopropanol), clarifying bY filtration and basifying with aqueous ammonia (10% excess) as described in Appendix A. The mixture is then stirred to allow the polymorph B to crystallise completely, then the product is isolated by filtration, washed well with water and dried to constant weight.

The invention is illustrated but in no way limited by the following examples. In the examples, all references to cimetidine refer to the B polymorph unless otherwise stated.

EXAMPLE 1

Cimetidine Suspension (200 mg in 10 ml)

| INGREDIENTS | QTY (g) | UNIT DOSE mg/10 ml |
|---|---|---|
| Cimetidine Base (B Polymorph) | 120.0 | 200 |
| Avicel RC591 | 90.0 | 150 |
| Water | 1500.0 | 2500 |
| Propylene Glycol | 300.0 | 500 |
| Glycerol | 300.0 | 500 |
| Butylparaben | 6.0 | 10 |
| Propylparaben | 3.0 | 5 |
| Sodium Saccharin | 2.4 | 4 |
| Vanilla (Firmenich 54.286C) | 3.0 | 5 |
| Cream (FDO FC 900772) | 6.0 | 10 |
| Titanium Dioxide 50% in Glycerol | 24.0 | 40 |
| Sorbitol 70% in water* | 4940.0 | 8234 |

*Sorbitol 3460 g, Water 1480 g.

PROCESS

The Avicel is dispersed in demineralised water using a low shear propeller mixer and the resulting dispersion is passed through a premier colloid mill (premier Colloid Mills Ltd., Walton-on Thames, Surrey, U.K.) on high speed at $25\mu$ gap. The Avicel high shear dispersion is mixed with 3.6 kg of the sorbitol 70% solution and to the mixture is added the glycerol followed by a solution of the parabens in propylene glycol. The flavourings and the titanium dioxide paste are then added with stirring to give a homogenous mixture. Cimetidine is then added followed by the remainder of the sorbitol to give a total volume of 6 liters. The batch is then passed through a colloid mill on low speed set to the smallest possible gap (approx $25\mu$) such that the milling process does not cause the temperature of the milled material to exceed 35° C. The pH of the resulting suspension is approximately 7.8.

EXAMPLE 2

Cimetidine Suspension (200 mg in 5 ml)

This has a similar composition to that described in Example 1 except that the quantity of cimetidine is doubled

EXAMPLE 3

Cimetidine Suspension in Hydrogenated Glucose Syrup

This has a composition analogous to that described in Example 2 except that instead of sorbitol 70%, an equivalent volume of hydrogenated glucose syrup (74% solids) is used as the vehicle.

EXAMPLE 4

Determination of the viscosities of the formulations of Examples 1 to 3, 6 and 8

The viscosities of the compositions of Examples 1 to 3, 6 and 8 were determined using a Rheomat 30 Rheometer supplied by Contraves of Switzerland. The measurements were conducted at 27° C. and the results are shown in Table 2.

TABLE 2

| Shear Rate (sec.$^{-1}$) | Apparent Viscosity ($\eta$a) (mPa · s) | | | |
|---|---|---|---|---|
| | Examples 1 and 2 | Example 3 | Example 6 | Example 8 |
| 0.7 | 700 | 1000 | 3400 | 1000 |
| 7 | 400 | 800 | 1000 | 500 |
| 70 | 200 | 300 | 500 | 200 |
| 700 | 100 | 200 | 300 | 100 |

EXAMPLE 5

Comparative Stabilities of Suspensions containing Polymorph A and Suspensions containing Polymorph B (i) Compositions as described in Example 1 were subjected to isothermal storage for one year at temperatures of 4°, 22°, 30° and 40° C. Microscopic examination after this time indicated that no crystal growth had occurred.

The composition of Example 1 was also subjected to 50 thermal cycles between 10° and 30° C. No crystal growth was detected following this test.

(ii) Compositions identical to :hose described in Example 1, except that cimetidine polYmorph A was used instead of cimetidine polymorph B, were also subjected to stability tests. The median particle size in the freshly prepared suspensions was approximately $40\mu$.

After 5 months at room temperature filaments 750μ in length were observed upon microscopic examination.

At ten months filaments up to 2.5 mm were observed along with filamentous clusters up to 1 mm in length.

Upon storage at 30° C. for 3 days, filaments up to 2.5 mm in length were observed and after storage at 40° C. for 3 days a large filamentous aggregate of 4 mm overall length was detected.

After thermal cycling, 10°-30° C., 9 cycles, numerous feather-like clusters up to 800μ long and 200μ wide were formed. One feather-like aggregate of 1.8 mm length was detected.

EXAMPLE 6

100 Mg Cimetidine/Sodium Alginate Suspension

| INGREDIENTS | UNIT DOSE QUANTITY (g/100 ml) |
| --- | --- |
| Cimetidine Base | 2.0 |
| Sodium Alginate (Protanal LFR 5/60) | 5.0 |
| Potassium Bicarbonate | 3.18 |
| Propylene Glycol | 5.0 |
| Glycerol | 5.0 |
| Avicel CL-611 (Microcrystalline cellulose and sodium carboxymethylcellulose) | 0.2 |
| Sorbitol Solution BP (70% w/w) | 22.0 |
| Hydrogenated Glucose Syrup (Lycasin 80/55) | 4.0 |
| Butylparaben | 0.1 |
| Propylparaben | 0.05 |
| Ethylenediaminetetraacetic acid (disodium salt) | 0.1 |
| Sodium dihydrogen orthophosphate dihydrate | 0.31 |
| Di-Sodium hydrogen orthophosphate dodecahydrate | 0.475 |
| Sodium Saccharin | 0.2 |
| Passion Fruit Flavour | 0.01 |
| Peppermint Flavour | 0.02 |
| Titanium Dioxide in 50% Glycerol | 0.8 |
| Demineralised Water | to 100 ml |

PROCESS

The hydroxybenzoates were dissolved in warm propylene glycol and to the resulting solution was added the glycerol. After the solution had cooled to room temperature, the cimetidine was added with stirring to give a smooth slurry.

A sodium alginate mixture was prepared by dissolving the disodium edetate in demineralised water and then dispersing the sodium alginate in the solution using a high shear homogeniser.

The cimetidine slurry sorbitol solution, hydrogenated glucose syrup and sodium alginate mixture were added to a dispersion of the Avicel in demineralised water and the resulting mixture was stirred until homogenous. The remaining ingredients were added, additional demineralised water being added as necessary to give the correct volume. Finally, the suspension was passed through a colloid mill set at low speed as described in Example 1.

EXAMPLE 7

200 mg/5 ml Cimetidine/Magnesium hydroxide/Aluminium hydroxide Suspension

| | g/100 ml | % (w/w) |
| --- | --- | --- |
| Cimetidine | 4 | 3.31 |
| Magnesium hydroxide | 4 | 3.31 |

-continued

| | g/100 ml | % (w/w) |
| --- | --- | --- |
| Aluminium hydroxide (as Al$_2$O$_3$) | 2.4 | 1.98 |
| Xanthan | 0.3 | 0.25 |
| Propylparaben | 0.05 | 0.041 |
| Butylparaben | 0.10 | 0.083 |
| Propylene glycol | 5.0 | 4.13 |
| Glycerol | 2.0 | 1.65 |
| Sorbitol (70%) | 75 | 62.0 |
| Water | to 100 ml. | |

EXAMPLE 8

100 mg/5 ml Cimetidine/Magnesium hydroxide/Aluminium hydroxide Suspension

| | g/100 ml | % (w/w) |
| --- | --- | --- |
| Cimetidine | 2 | 1.65 |
| Magnesium hydroxide | 4 | 3.31 |
| Aluminium hydroxide (as Al$_2$O$_3$) | 2.4 | 1.98 |
| Xanthan | 0.3 | 0.25 |
| Propylparaben | 0.05 | 0.041 |
| Butylparaben | 0.10 | 0.083 |
| Mint Flavouring | 0.10 | 0.083 |
| Propylene Glycol | 5.0 | 4.13 |
| Glycerol | 2.0 | 1.65 |
| Sucrose | 35 | 28.9 |
| Sorbitol (70%) | 25 | 20.7 |
| Water | to 100 ml. | |

EXAMPLE 9

100 mg/5 ml Cimetidine/Calcium Carbonate Suspension

| | g/100 ml | % (w/w) |
| --- | --- | --- |
| Cimetidine | 2 | 1.51 |
| Calcium carbonate | 11.7 | 8.86 |
| Avicel RC591 | 1.5 | 1.14 |
| Propylparaben | 0.05 | 0.038 |
| Butylparaben | 0.10 | 0.076 |
| Sodium saccharin | 0.04 | 0.030 |
| Vanilla } Flavours | 0.05 | 0.038 |
| Cream | 0.10 | 0.076 |
| Titanium dioxide (50%) | 0.4 | 0.30 |
| Propylene glycol | 5.0 | 3.78 |
| Glycerol | 5.0 | 3.78 |
| Water | 25 | 18.93 |
| Lycasin (hydrogenated glucose syrup) | to 100 ml | 61.42 |

EXAMPLE 10

Cimetidine/Calcium carbonate/Magnesium hydroxide Suspensions

| | g/100 ml | (w/w) |
| --- | --- | --- |
| Cimetidine | 2 | 1.5 |
| Calcium Carbonate | 10 | 7.52 |
| Magnesium hydroxide | 1 | 0.75 |
| Avicel RC591 | 1.5 | 1.13 |
| Propylparaben | 0.05 | 0.038 |
| Butylparaben | 0.10 | 0.075 |
| Sodium Saccharin | 0.04 | 0.03 |
| Vanilla } Flavours | 0.05 | 0.038 |
| Cream | 0.10 | 0.075 |
| Titanium dioxide (50%) | 0.4 | 0.30 |
| Propylene glycol | 5.0 | 3.76 |
| Glycerol | 5.0 | 3.76 |
| Water | 25 | 18.79 |

| -continued | | |
|---|---|---|
| | g/100 ml | (w/w) |
| Lycasin (hydrogenated glucose syrup) | to 100 ml | 62.24 |

APPENDIX A

Preparation of Cimetidine Polymorph B

To a stirred suspension of 252 grams of cimetidine polymorph A in 2.0 liters of water and 250 ml of isopropanol was added a solution containing 60 grams of acetic acid in 125 ml water. The mixture was stirred and the resulting solution was clarified by filtration. To the resulting clear solution was added with agitation a solution containing 68 ml of concentrated ammonia (27% w/w) in 125 ml of water. Following precipitation of the cimetidine base, the mixture was heated to 40°–45° C., and held there for 24 hours. The appropriate in-process checks* after this time indicated that the solid was completely form "B". The mixture was cooled, the product isolated by filtration, and washed well with water. The solid was dried at 60° C. to yield 240 grams (95%) of crystalline cimetidine "B" having a melting point of 142.5°–144° C. * An appropriate process check is to obtain an infra-red spectrum of the product and calculate the ratio of the peak heights of the absorbance bands at 1004 and 993 cm$^{-1}$. The concentration of polymorph C is then determined by reference to a calibration curve obtained by plotting the peak ratios for various standard mixtures of polymorph C and polymorph B.

The above-mentioned process for preparing cimetidine polymorph B is also disclosed and is claimed in a co-pending European patent Application which derives priority from British patent Application No. 8618846 filed on 1st August 1986. The term "polymorph B" as used hereinabove includes a reference to crystalline cimetidine prepared according to the said process.

What is claimed is:

1. A stable pharmaceutical composition suitable for oral administration comprising a suspension of an effective histamine H2-antagonist amount of particulate cimetidine in an aqueous phase wherein substantially all of the cimetidine present is of the polymorphic B form.

2. A composition according to claim 1 wherein at least 95% of the cimetidine is in the polymorphic B form.

3. A composition according to claim 1 having a pH in the range 7–9.5.

4. A composition according to claim 1 wherein the viscosity of the suspension, as measured at 25° C. and at a shear rate of 0.7 sec$^{-1}$, is in the range 200 mPa.s to 1.500 mPa.s.

5. A composition according to claim 4 wherein the viscosity is 500 mPa.s to 1.200 mPa.s.

6. A composition according to claim 1 which contains a suspending agent.

7. A composition according to claim 6 wherein the suspending agent is a mixture of sodium carboxymethylcellulose and microcrystalline cellulose, which mixture is present in an amount in the range of from about 0.6 to about 1.5% w/w of the total weight of the composition.

8. A composition according to claim 1 wherein at least 80% of the cimetidine particles have an apparent diameter in the range of from about 5$\mu$ to about 200$\mu$.

9. A composition according to claim 1 which contains an antacid or alginate.

10. A composition according to claim 1 containing 1.5–3.5% w/w of cimetidine, 35–15% w/w of water, 35–55% w/w of sorbitol, 0–10% w/w of a humectant selected from the group consisting of propylene glycol or glycerol and 0.6–1.5% w/w of a mixture of sodium carboxymethyl cellulose and microcrystalline cellulose.

11. A composition according to claim 9 which contains EDTA or a salt thereof in an amount from about 0.05% w/w to about 0.1% w/w of the total weight of the composition.

12. A composition according to claim 1 wherein at least 90% of the cimetidine is in the polymorph B form.

13. A process for producing a stable pharmaceutical composition comprising dispersing a suspending agent with a substantially pure effective amount of histamine H2 antagonist Polymorph B cimetidine into a suspension such that the viscosity of the resulting suspension is less than 1500 mPa's and greater than 200 mPa's.

14. A stable pharmaceutical composition, which is readily pourable, suitable for oral administration comprising a suspension of an effective histamine H2-antagonist amount of a particulate cimetidine in an aqueous phase wherein substantially all of the cimetidine present is of the polymorphic B form.

15. A composition according to claim 14 wherein the resulting viscosity of the suspension, as measured at 25° C. and at a shear rate of 0.7 sec$^{-1}$, is in the range of 200 mPa's to 1,500 mPa's.

16. A stable pharmaceutical composition suitable for oral administration comprising an alginate, and a suspension of an effective histamine H2-antagonist amount of a particulate cimetidine in an aqueous phase wherein substantially all of the cimetidine present is of the polymorphic B form.

* * * * *

UNITED STATES PATENT AND TRADEMARK OFFICE
CERTIFICATE OF CORRECTION

PATENT NO. : 4,996,222

DATED : February 26, 1991

INVENTOR(S) : Carlin et al.

It is certified that error appears in the above-identified patent and that said Letters Patent is hereby corrected as shown below:

In column 1, line 20; change "polYmorphism" to -- polymorphism --.

In column 1, line 21; change "polYmorphic" to -- polymorphic --.

In column 1, line 41; change "unpleaSant" to -- unpleasant --.

In column 1, line 62; change "lumpY" to -- lumpy --.

In column 2, line 1; change "Various" to -- various --.

In column 2, line 32; change "Will" to -- will --.

In column 3, line 8; change "suspendinq" to -- suspending --.

In column 4, line 7; change "W/w" to -- w/w --.

In column 4, line 34; change "i$" to -- is --.

In column 5, line 36; change "bY" to -- by --.

In column 6, line 64; change ":hose" -- those --.

UNITED STATES PATENT AND TRADEMARK OFFICE
CERTIFICATE OF CORRECTION

PATENT NO. : 4,996,222
DATED : February 26, 1991
INVENTOR(S) : Carlin et al.

It is certified that error appears in the above-identified patent and that said Letters Patent is hereby corrected as shown below:

In column 9, line 43; change "H2" to -- $H_2$ --.

In column 10, line 4; change "1.200" to -- 1,200 --.

In column 10, line 23; change "claim 9" to -- claim 16 --.

Signed and Sealed this

Thirteenth Day of April, 1993

Attest:

STEPHEN G. KUNIN

*Attesting Officer*     *Acting Commissioner of Patents and Trademarks*